United States Patent
Costa Ribalta et al.

(10) Patent No.: US 8,515,531 B2
(45) Date of Patent: Aug. 20, 2013

(54) METHOD OF MEDICAL MONITORING

(75) Inventors: Alejo Costa Ribalta, Stuttgart (DE); Rainer Schluess, Bondorf (DE); Bernd Wilm, Rohrdorf (DE)

(73) Assignee: Koninklijke Philips Electronics N.V. (NL)

(*) Notice: Subject to any disclaimer, the term of this patent is extended or adjusted under 35 U.S.C. 154(b) by 1724 days.

(21) Appl. No.: 11/575,505

(22) PCT Filed: Sep. 9, 2005

(86) PCT No.: PCT/IB2005/052948
§ 371 (c)(1),
(2), (4) Date: Mar. 19, 2007

(87) PCT Pub. No.: WO2006/033038
PCT Pub. Date: Mar. 30, 2006

(65) Prior Publication Data
US 2009/0275846 A1 Nov. 5, 2009

(30) Foreign Application Priority Data
Sep. 24, 2004 (EP) .................................... 04104645

(51) Int. Cl.
*A61B 5/04* (2006.01)

(52) U.S. Cl.
USPC ............................................ 600/512; 600/523

(58) Field of Classification Search
USPC .................................................. 600/512, 523
See application file for complete search history.

(56) References Cited

U.S. PATENT DOCUMENTS

| | | | |
|---|---|---|---|
| 3,811,040 A | 5/1974 | Weinfurt et al. | |
| 6,282,440 B1 * | 8/2001 | Brodnick et al. | 600/512 |
| 2004/0111021 A1 * | 6/2004 | Olson | 600/407 |

* cited by examiner

Primary Examiner — Tammie K Heller

(57) ABSTRACT

A method of medical monitoring using data collected by a number of sensors, wherein the position of the sensors form a predefined arrangement and collected data depend on the position of the sensor on the patient. The method includes displaying data using a number of multiaxis diagrams where the position of the axes is related to the position of the sensors in the predefined arrangement, and on each axis data from its related sensor is displayed. Further, a multiaxis diagram is used, wherein each axis represents a particular dimension of data and spatial information is displayed in addition to the pure values. With this additional information a two- or three-dimensional representation and localization of data is provided. The technique allows a more effective recognition of monitored data and enables physicians to perform a fast pattern recognition to recognize and evaluate a patient's situation in a quicker and more effective way.

6 Claims, 6 Drawing Sheets

METHOD OF MEDICAL MONITORING

The present invention relates to a method of medical monitoring, a medical monitoring system and a computer program to control a medical monitoring system.

Patient monitors are used for the observation of the condition of the patient. Today these monitors can display more than hundred different parameters and trigger alarm signals in case one or some of them shows an undesired behavior. Due to the large amount of displayed parameters it is sometimes difficult for a physician to quickly recognize a critical or undesired situation of the patient. The human bounded perception capabilities, worsen by the stress resulted from extreme medical situations like in operation procedures for example, hinder the complete perception of all the information offered by such monitors. To avoid this problem, improvements in the field of graphical representation of medical data are being sought. Known methods try to represent the medical information in a meaningful way in order to reach a quicker recognition and evaluation of the patient's situation. For example in the U.S. Pat. No. 3,811,040 a method is disclosed, wherein equiangularly spaced vectors are displayed, and the vectors correspond respectively with physiological parameters such as heart rate, blood pressure and others and the end of the vectors are connected to form a contour on a display screen.

It is an object of the present invention to provide an improved monitoring technique that allows a more effective recognition of monitored data.

This object is achieved according to the invention by a method of medical monitoring using data collected by a number of sensors, the sensors are positioned on a patient in a way that the sensors form a predefined arrangement and the collected data depend on the position of the sensor on the patient. The method comprises the step of displaying data using a number of multiaxis diagrams in which the position of the axes is related to the position of the sensors in the predefined arrangement, and on each axis data from its related sensor is displayed. The data displayed may include data derived directly from the sensors, e.g. electric voltages, or data derived from calculations based on them. Thereby the term "displaying" includes the use of a display screen, e.g. a medical monitor, the use of printer to produce a print etc.

The object of the present invention is also achieved by a medical monitoring system, the system comprises a number of sensors which can be positioned on a patient in a way that the sensors form a predefined arrangement, the sensors are adapted to collect data, which depend on the position of the sensors on the patient. The system further comprises a device adapted to display data using a number of multiaxis diagrams in which the position of the axes is related to the position of the sensors in the predefined arrangement and on each axis data from its related sensor is displayed.

The object of the present invention is also achieved by a computer program comprising computer instructions adapted to control the medical monitoring system when the computer program is executed in a computer. The computer program comprises computer instructions to display data using a number of multiaxis diagrams, in which the position of the axes of the diagram is related to the position of the sensors in the predefined arrangement and on each axis data from its related sensor is displayed. The technical effects necessary according to the invention can thus be realized on the basis of the instructions of the computer program in accordance with the invention. Such a computer program can be stored on a carrier such as a CD-ROM or it can be available over the internet or another computer network. Prior to executing the computer program is loaded into the computer by reading the computer program from the carrier, for example by means of a CD-ROM player, or from the internet, and storing it in the memory of the computer. The computer includes inter alia a central processor unit (CPU), a bus system, memory means, e.g. RAM or ROM etc., storage means, e.g. floppy disk or hard disk units etc. and input/output units.

A core idea if the invention is to present the data in a way that allows a fast detection of data in its spatial situation. For this purpose data is displayed in consideration of the spatial position of the sensors, which from which the data is obtained.

Whereas known monitoring techniques merely display medical data on axes which are defined in a more or less arbitrary way, the present invention suggests to use a multi-axis diagram in a way, that each axis represents the particular spatial orientation of the data. In other words not only the pure values, but additional spatial information are displayed and provided to a user, e.g. to a physician. With this additional information a two- or even three-dimensional representation of data and therefore a localization of data is provided. The monitoring technique according to the invention thus allows a more effective recognition of monitored data. Physicians are enabled to carry out a fast pattern recognition in order to recognize and to evaluate the situation of the patient in a quicker and more effective way.

These and other aspects of the invention will be further elaborated on the basis of the following embodiments which are defined in the dependent claims.

The present invention may be used for any medical monitoring technique using data collected by a number of sensors, the sensors are positioned on a patient in a way that the sensors form a predefined arrangement and the collected data depend on the position of the sensor on the patient. In a preferred embodiment of the present invention the invention is employed with an Electrocardiogram (ECG), thus the sensors are ECG electrodes and the collected data are ECG data. The electrodes are positioned in a certain arrangements, e.g. to provide a continuous 12-lead ECG monitoring obtaining three "Einthoven" extremity leads, three "Goldberger" extremity leads and six "Wilson" chest-leads. The invention can also be used with an Electroencephalogram (EEG) in order to monitor the electrical activity of the brain via electrodes applied to the patient's scalp. In case the invention is used for an ECG monitoring, preferably ST elevation values are displayed. These ST values result from the projection of the heart's electrical vector in each one of the lead's axis. A physician may use ST segment deviation for detecting myocardial ischemia. Other values, which may be used for displaying are for example: P point value, Q point value, R point value etc.

An ECG analyzes the electrical activity of the heart by means of the projection of three-dimensional electrical values in two orthogonal planes, namely the horizontal plane and the vertical plane. ECG data obtained by an electrode represent a projection of the cardiac electrical field in a two-dimensional subspace. In order to display this areal or spatial information according to a further embodiment of the invention data is displayed using two multiaxis diagrams and the first diagram comprises axes related to vertical leads and the second diagram comprises axes related to horizontal leads.

According to another embodiment of the invention a multidimensional representation of data is displayed, the representation is obtained by a connection of values displayed on a number of axes. In other words a graphical object is formed by connecting the current values to be displayed on a number of axes. This graphical object serves as a figure or pattern, which may be used as base for the recognition of diseases. If the pattern is graphically accentuated in a way that the graphical object is displayed as a continuous area preferably using conspicuous colors, the shape and size of the pattern can be recognized in a very short time.

In still another embodiment of the invention it is advantageous to provide e.g. a two or three-dimensional scheme to obtain a more realistic impression of the patient's situation. In this case a two or three-dimensional picture preferably of that part of the patient's body on which the sensors are positioned (e.g. the heart of the patient) is displayed together with a two- or three-dimensional representation of data obtained by a number of sensors. In other words a more or less realistic picture is used in order to observe more accurately a two- or three-dimensional reconstruction of the values represented in the diagram(s). In case of ECG the reconstruction is preferably calculated by means of a spatial interpolation between the values in all axes. The picture of the patient's body or part of that body may be a real picture taken from the patient to be monitored, e.g. by means of an ultrasonic device etc. Alternatively a patient-independent and schematic model is used.

In still another preferred embodiment of the invention only data, e.g. the multidimensional representation or pattern, is displayed, whereas the multiaxis diagrams are not displayed. In other words the diagrams remain invisible to the user.

These and other aspects of the invention will be described in detail hereinafter, by way of example, with reference to the following embodiments and the accompanying drawings; in which.

Figure 1:
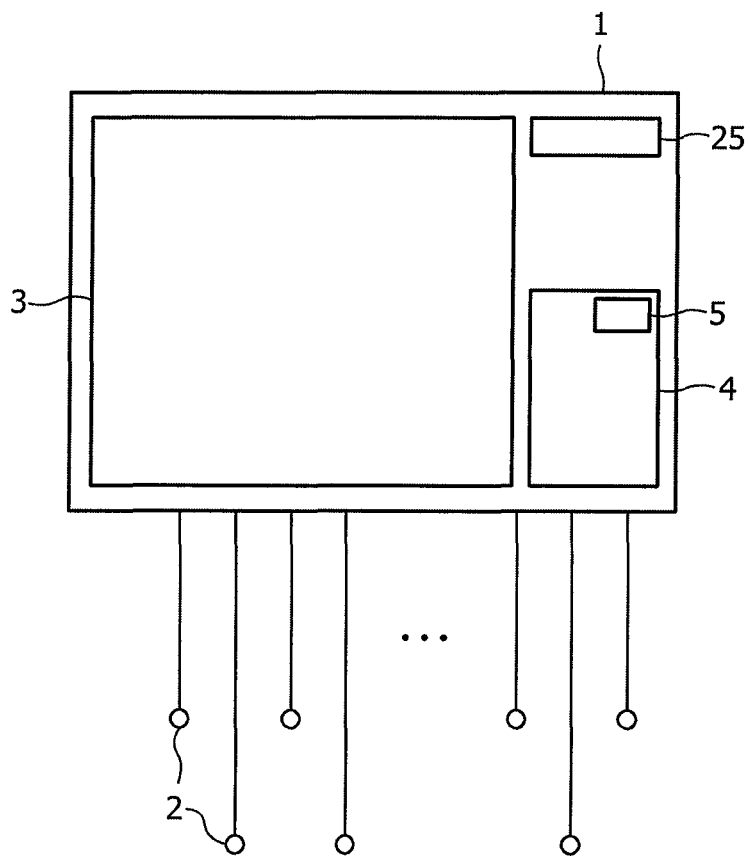
FIG. 1 shows a schematic block diagram of a monitoring system.

In the following embodiment an electrocardiographic monitoring system is used to illustrate the present invention. The monitoring system 1 comprises a number of ECG electrodes 2 to be positioned on a patient (not shown) and a patient monitor 3, e.g. a digital storage oscilloscope or a LED flat screen monitor etc. The system 1 further comprises a control device 4 adapted to read the sensed data, to calculate according to defined ECG control and analysis algorithms and to control the monitor 3 and the displayed information. The control device 4 comprises a computer with a processor 5 adapted for executing a computer program comprising computer instructions adapted to control the medical monitoring system 1 when the computer program is executed in the computer.

Routine ECG monitoring is standard practice in coronary and intensive care units, emergency rooms, ambulatory monitoring settings and operating rooms. In the present embodiment a continuous ST segment monitoring is carried out in order to detect ST changes which may indicate ischemic episodes. Data obtained from such a monitoring are automatically displayed on the monitor 3 to show a physician the status of the patient. For carrying out an ECG test, a variable number of ECG electrodes 2 are positioned on a patient in a way that the electrodes form a predefined arrangement, e.g. accordingly to "Einthoven", "Goldberger" and "Wilson", EASI, "Frank" or others. According to the present invention multiaxis diagrams are used for graphical representation of monitored data.

Figure 2:
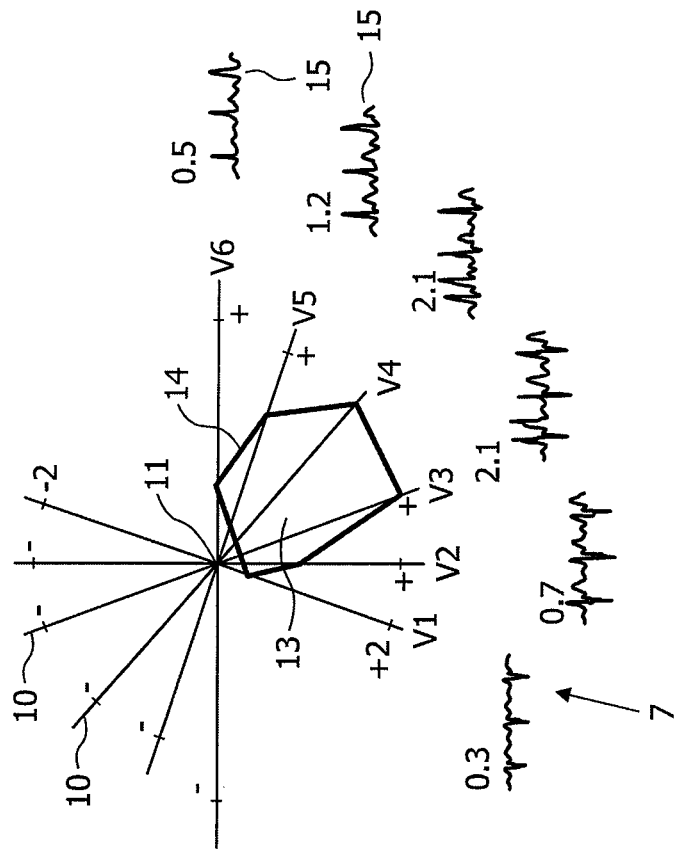
FIG. 2 shows multiaxis diagrams representing ST values.
Figure 2:
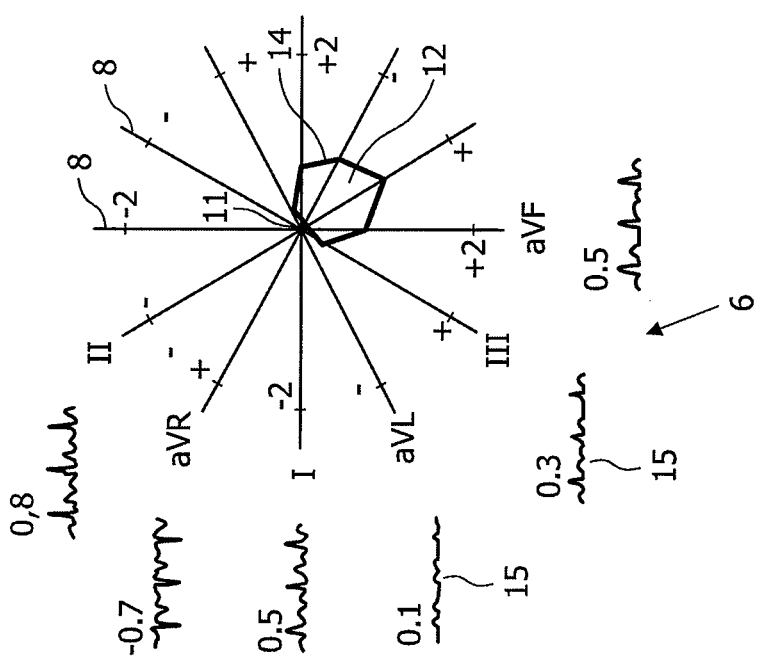

In FIG. 2 two such multiaxis diagrams 6, 7 are depicted as they are displayed on the monitor 3. The diagrams 6, 7 are used to represent the ST lead values of a common 12-Lead ECG as a three-dimensional view. The representation is not limited to these twelve ECG leads. Any ECG lead or other ECG related parameter may be used.

The diagram 6 on the left hand side represents the vertical plane of the two-dimensional subspace in which the cardiac electrical field of the heart is projected. Therefore this diagram 6 consists of six axes 8 representing the six vertical ST leads of a 12-lead-ECG, namely aVF, III, aVL, I, aVR and II (clockwise). Thereby the bipolare "Einthoven" leads I, II and II and the unipolare "Goldberger" leads aVR, aVL and aVF are used. The displayed values are obtained from the mathematical linear combination of the values of the electrical tensions obtained from the ECG electrodes 2 listed above. The position of the axes 8 and its angle represent the location of its corresponding ECG electrode 2 on the patient's body during the ECG test. Thereby the following scheme is applied:

| Axis | angle |
|------|-------|
| I    | 0°    |
| II   | 60°   |
| III  | 120°  |
| aVR  | −150° |
| aVL  | −30°  |
| aVF  | 90°   |

The diagram 7 on the right hand side represents the horizontal plane and therefore consists of six axes 10 relating to the six horizontal "Wilson" ST leads of a 12-lead-ECG, namely V6, V5, . . . , V1 (clockwise) are used. Again the position of these axes 10 and its angle represent the location of its corresponding ECG electrode 2 on the patient's body during the ECG test. Thereby the following scheme is applied:

| Axis | angle |
|------|-------|
| V1   | 120°  |
| V2   | 90°   |
| V3   | 75°   |
| V4   | 60°   |
| V5   | 30°   |
| V6   | 0°    |

In other words the real positions of the twelve ECG leads are transferred to a displaying model. Each axis 8, 10 of the diagrams 6, 7 is assigned to one parameter. In both diagrams 6, 7 all axes 8, 10 run from negative values to positive values (or vice versa) through a zero-point 11. The directions of the axes 8, 10 are shown using "+" and "−" signs nearby the axes. For example the aVF axis leading downwards from the center of the diagram 6 represent positive values, whereas the aVL axis leading in the lower left corner of the diagram 6 represent negative values.

The values displayed on the six axes 8, 10 in each diagram 6, 7 are connected in order to form a colored polygonal pattern 12, 13, which may be used for easy recognition of the patient's situation. The graphical display is accentuated by a thick colored line 14 bordering the area of the pattern 12, 13. The shape of the pattern 12, 13 gives information not only about the current values of the ST leads but also about the spatial arrangement of the ECG data. For example from the right hand side diagram 7 in FIG. 2, which illustrates the horizontal plane, it can be seen, that a possible ischemic disease may be located within the fore side of the heart. From the diagram 6 on the left hand side, which illustrates the vertical plane, it can be seen, that a possible disease may be located in a lower region of the heart. Both diagrams 6, 7 together give the full three-dimensional information, that the disease may be most likely located in a lower region of the fore side of the patient's heart. These display functions and all display functions described furthermore within this description are controlled by means of the control device 4. The axes used in order to present the data on the monitor have not necessarily to be displayed. In a preferred embodiment only the pattern is displayed, whereas the axes remain "invisible".

Additionally, further information concerning the represented values is displayed at the end of the axes 8, 10. This seeks to clarify and extend the comprehension of the information they provide. In FIG. 2, near every axis 8, 10, a PQRST complex 15 (so called ST snippet) of the corresponding lead is placed. It is meant to offer further information on the ST value represented on the axes. Above each ST snippet 15 the value of the ST elevation or depression is displayed.

Since continuous ST segment monitoring is a very important part of the routine ECG, the present invention is particularly useful to detect possible diseases reflected with a variation in the ST segments like for example: ischemic heart disease, acute pericarditis, left ventricular hypertrophy, left bundle branch block, advanced hyperkalemia, hypothermia, some cases of mitral valve prolapsed, etc. Since ischemic heart disease is one of the most critical diseases in view of its serious mortality and frequency of occurrence, the importance of supporting, improving and accurately presenting data derived from the ST segments has become critical in modern monitoring. Although monitoring ECG for ST segment deviation is not the most sensitive for myocardial ischemia detection, it remains the only practical technique for continuous non-invasive monitoring of ischemic episodes.

Figure 3:
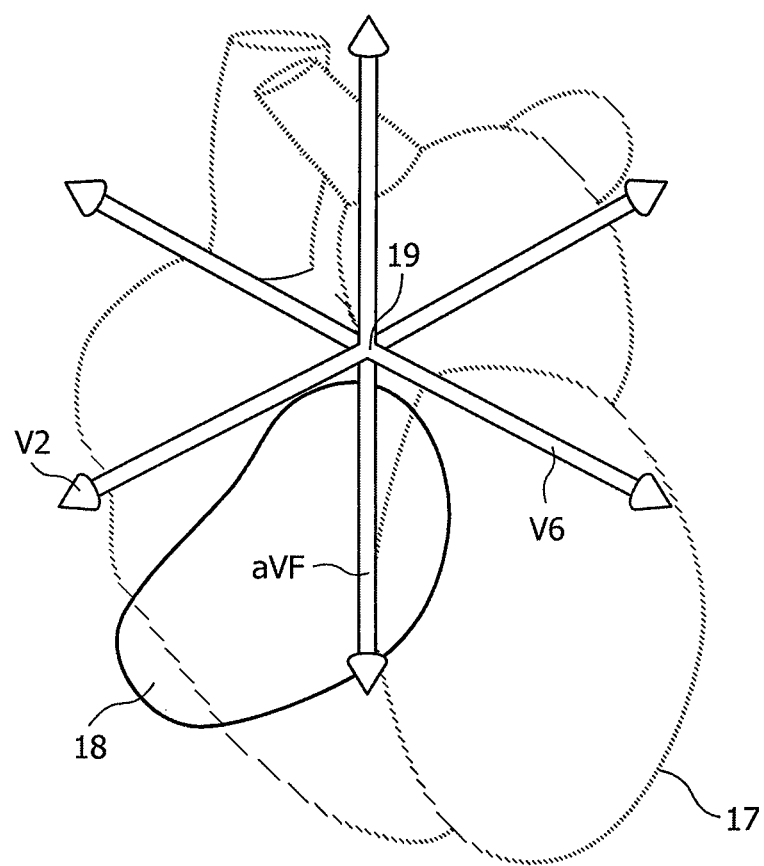
FIG. 3 shows a schematic three-dimensional heart with a resulting three-dimensional reconstruction of the two-dimensional projected values.

In another embodiment of the invention a three-dimensional scheme is provided to obtain a more realistic impression of the patient's situation. As illustrated in FIG. 3 a three-dimensional picture of a schematic three-dimensional heart model 17 is displayed. Preferably the heart model 17 is displayed on the same monitor 3 together with the two multiaxis diagrams 6, 7. Within the heart model 17 preferably a three-dimensional reconstruction 18 of the values of some selected leads, all leads or linear combination of a number of leads is displayed. In another embodiment (not shown) a vector is displayed pointing to the mass center of this three-dimensional reconstruction 18. This three dimensional reconstruction 18 in form similar to an ellipsoid is preferable calculated by means of an interpolation of the values projected in the planes. The three axes reflect the three orthogonal spatial dimensions of a given Cartesian coordinate system. The center 19 of the diagram is set in the center of the heart model 17 in order to better recognize the location of the possible disease.

In order to allow a better understanding of the display, the heart model 17 can be rotated in a way that it can be seen from different perspectives depending on the physician wishes. This preferred embodiment illustrates a way to graphically represent in a patient monitor 3 the results of an ECG, based on multiaxis diagrams of both planes, horizontal and vertical, together with its three-dimensional reconstruction and provides a very effective way of data recognition.

Figure 4:
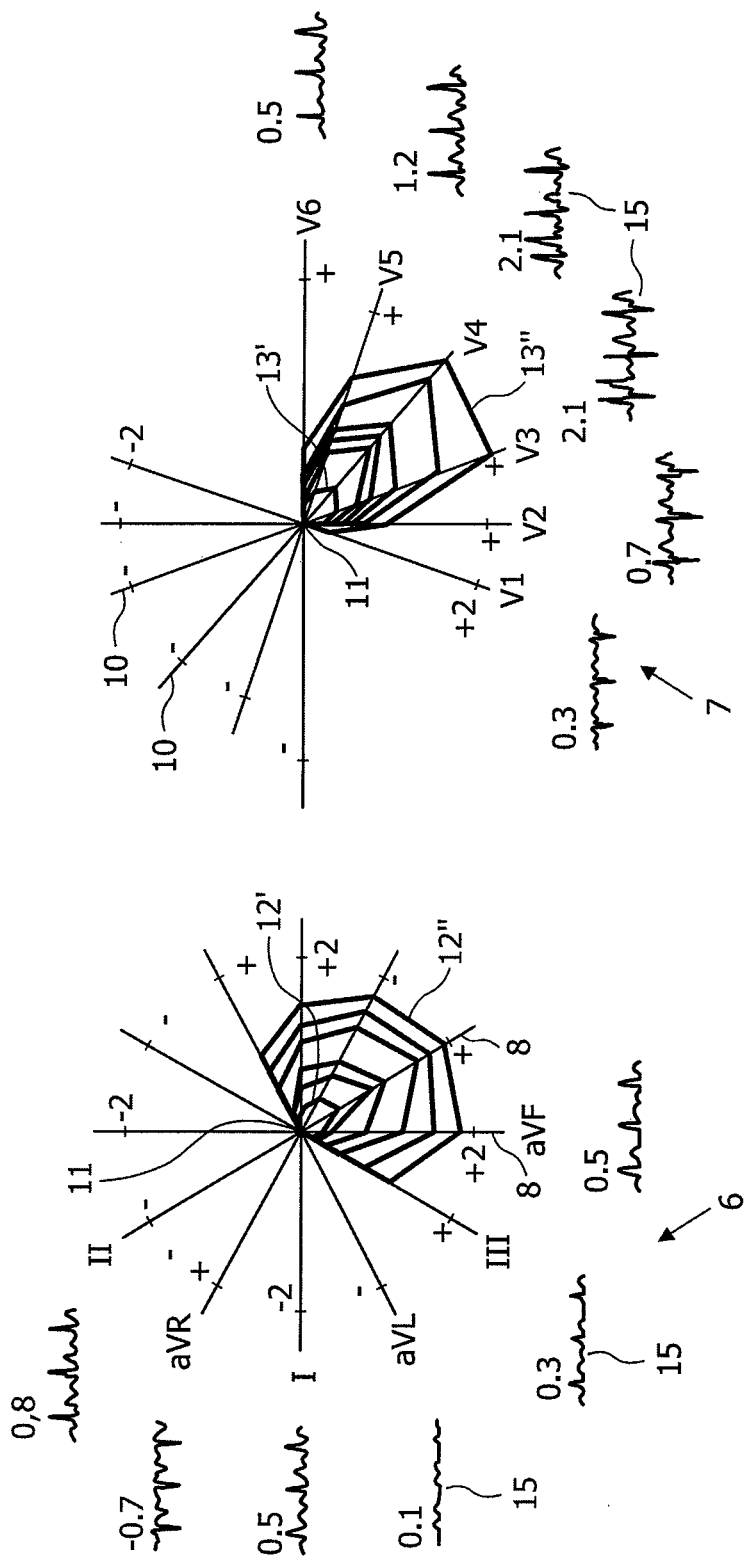
FIG. 4 shows multiaxis diagrams with past data for retrospective analysis.

In the normal modus, the information contained in the diagrams 6, 7 and in the heart model scheme 17 might be updated in real-time, providing to the physician a permanent assessment of the status of the patient. In a further embodiment a review of historical data is provided. In a retrospective modus the physician may review past representations of the pattern 12, 13 together with the additional axis information 15 (snippets) and with the schematic heart model 17. In still another embodiment the graphical representation includes another kind of retrospective analysis, in which a number of representations of past patterns 12, 13 are displayed simultaneously. In this case the displayed pattern is modified in each iteration in a way that illustrates its correspondence to a given point of time. A time window is defined, by means of a starting and an ending time and the information included within this range is displayed concurrently. The user is able to set this time window through a user interface (not shown). In FIG. 4 a possible implementation of the concept is shown. In this embodiment the area of the pattern 12, 13 is not filled. Using a fading out effect for the pattern 12, 13, e.g. from light yellow to dark yellow, the time perspective is displayed. The particular coloration of every pattern indicates the point of time its data belongs to. The brighter the pattern is, the closer it is to the present time. In the example the earliest pattern 12', 13' and the latter pattern 12", 13" are displayed simultaneously together with other "intermediate" pattern. Preferably, different screen buttons on the bottom of the monitor 3 facilitate the operation of browsing along the time dimension (not shown).

Figure 5:
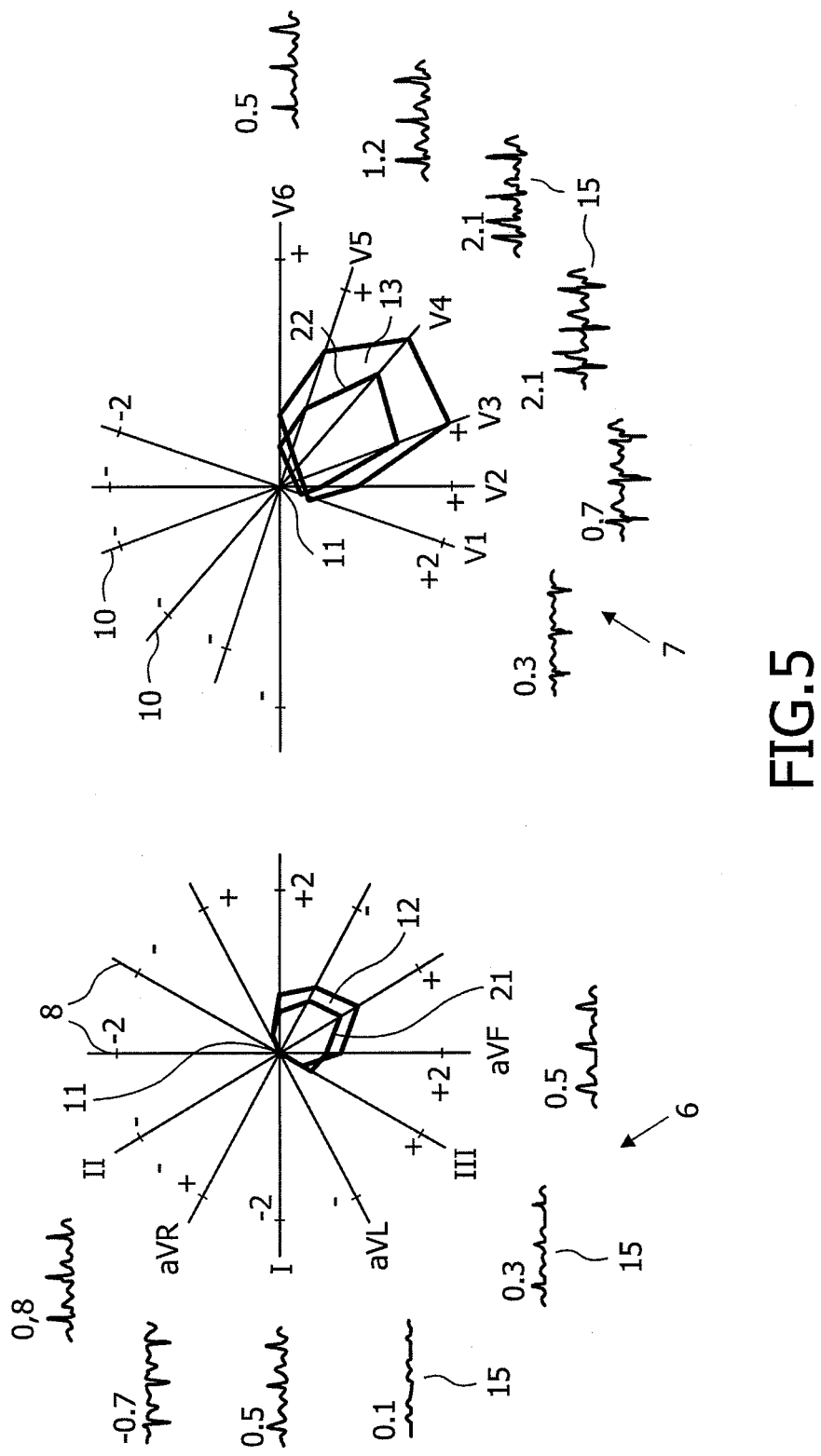
FIG. 5 shows multiaxis diagrams with reference information.

In a further embodiment illustrated in FIG. 5 a reference information is set by the user or automatically and displayed as a basis for comparison or development of values over time. This reference information is graphically represented in a distinctive pattern 21, 22 displayed in a brighter color in order to be clearly identified from the normal pattern 12, 13. The reference pattern 21, 22 can for example correspond to a snapshot of the values at a specific point of time. Since both static values and also the development of the difference over time can be an indication for the status and evolution of the disease, both presentations are available.

In another embodiment of the invention two parameters Q and C are defined as described by the following equations:

$$Q_{ECG} = \sum_{i=1}^{M} \sum_{j=1}^{M} a_{ij} \cdot ECG_i \cdot ECG_j$$

$$C_{ECG} = \sum_{i=1}^{M} \sum_{j=1}^{M} \sum_{k=1}^{M} a_{ijk} \cdot ECG_i \cdot ECG_j \cdot ECG_k$$

These parameters embrace any possible linear combination of all the quadratic (first equation) and cubic (second equation) permutations of the values from the ECG leads or any linear combination of them. The values of the coefficients "$a_{ij}$" and "$a_{ijk}$" represent the weight of each one of the permutations and can equal zero, case that would cancel the corresponding factor. M corresponds to an integer number equal to the total amount of leads (measured or calculated) from the electrocardiogram. In a preferred embodiment these ECG values will be the ST elevations. This results in the following equations:

$$AreaST = \sum_{i=1}^{M}\sum_{j=1}^{M} a_{ij} \cdot ST_i \cdot ST_j$$

$$VolumeST = \sum_{i=1}^{M}\sum_{j=1}^{M}\sum_{k=1}^{M} a_{ijk} \cdot ST_i \cdot ST_j \cdot ST_k$$

Figure 6:
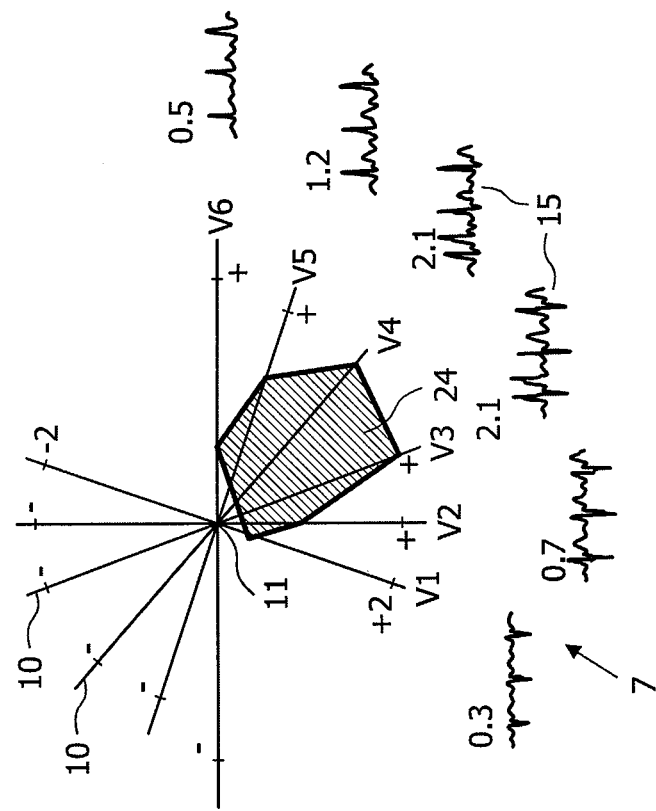
FIG. 6 shows multiaxis diagrams with alarm information.
Figure 6:
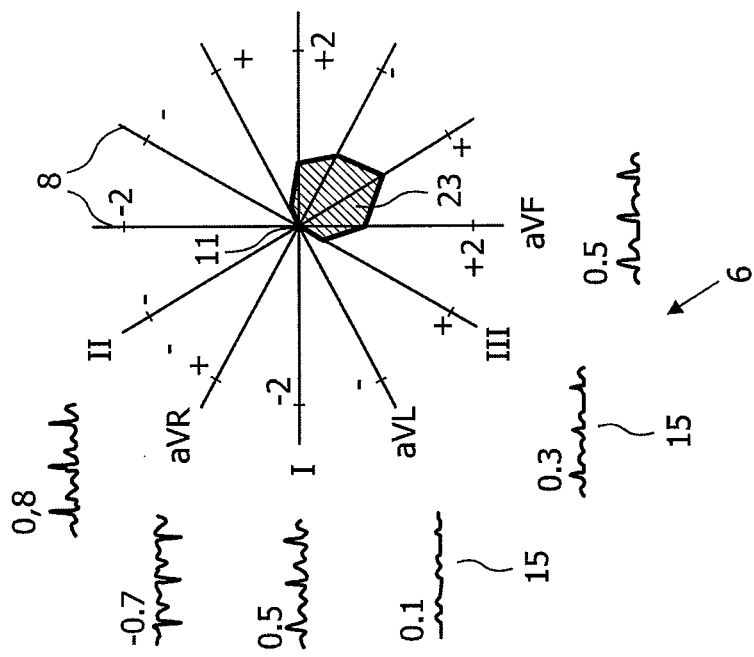

These equations represent any possible area (like the pattern 12, 13 described above) or any possible volume described by the spatial distribution of the ST parameters. In a preferred embodiment this area will be the area of the pattern in the first case ("AreaST") and the three-dimensional volume ("VolumeST") in the second case. The AreaST 23, 24 corresponding to the areas of the pattern 12, 13 in diagrams 6, 7 are shown in FIG. 6 and the VolumeST corresponding to the volume of the 3D reconstruction 18 shown in FIG. 3. The coefficients "$a_{ij}$" will be then the ones that allow the calculation of the pattern's area and the "$a_{ijk}$" the ones used to calculate the volume of the three-dimensional representation.

According to this embodiment an alarm in the monitor may be triggered each time a parameter 23, 24 exceeds or falls below a relative deviation or a given threshold or, in general, if a parameter follows a predefined behaviour during a given time.

The medical monitoring system 1 according to the invention is not only adapted to display the ECG data in the inventive way as described above. The system also allows printing and recording of the graphical information. Besides the numeric figures all graphical representations, e.g. pattern, axis extra information and schematic heart may furthermore be presented on a printout of the monitor 3. For this purpose the system 1 comprises an input/output device 25. The device 25 is furthermore adapted for transferring ECG and control algorithms from external sources, e.g. a CD-ROM device or a personal computer, to the system 1.

The present invention improves the speed, the reliability and the effectiveness of the recognition of electrical related heart diseases. By means of pattern recognition techniques it allows a quicker identification of heart diseases and fosters an early reaction from the care provider. In other words, the new type of representation as described before improves the accuracy as well as the speed of recognition of an electrical abnormality of the heart.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" does clot exclude a plurality, and that a single element, such as a computer system or another unit may fulfil the functions of several means recited in the claims. Any reference signs in the claims shall not be construed as limiting the claim concerned.

| REFERENCE LIST | |
|---|---|
| 1 | monitoring system |
| 2 | ECG electrode |
| 3 | patient monitor |
| 4 | control device |
| 5 | processor |
| 6 | multiaxis diagram for vertical plane |
| 7 | multiaxis diagram for horizontal plane |
| 8 | axis for vertical plane |
| 9 | free |
| 10 | axis for horizontal plane |
| 11 | zero point |
| 12 | pattern for vertical plane |
| 13 | pattern for horizontal plane |
| 14 | border line |
| 15 | ST snippet |
| 16 | free |
| 17 | heart model |
| 18 | three-dimensional reconstruction |
| 19 | center |
| 20 | free |
| 21 | reference pattern for vertical plane |
| 22 | reference pattern for horizontal plane |
| 23 | AreaST for vertical plane |
| 24 | AreaST for horizontal plane |
| 25 | input/output device |

The invention claimed is:

1. A method of displaying ECG lead signals representing a projection of the cardiac electrical field, using data collected by a number of sensors, the sensors being positioned on a patient in a way that the sensors form a predefined arrangement and the collected data depends on the position of the sensors on the patient, comprising:
   forming a graphical display of angularly positioned axes extending from a common heart reference point, the angle of each axis corresponding to the location of a different ECG lead on the body of a patient, with points on each axis corresponding to magnitude values of the corresponding ECG lead signal;
   acquiring a first plurality of different ECG lead values having a common acquisition time;
   identifying points on a plurality of the axes corresponding to the ECG lead values corresponding to each axis; and
   displaying the graphical display with the ECG lead values identified on the axes.

2. The method as claimed in claim 1, wherein the sensors are ECG electrodes.

3. The method as claimed in claim 1, wherein the displayed values are ST elevation values.

4. The method of claim 1, wherein forming further comprises forming a graphical display of angularly positioned axes extending from a common heart reference point which is a zero-point for each axis and each axis runs from negative magnitude values, through the zero-point, and to positive magnitude values.

5. The method of claim 1, further comprising:
   connecting the identified points on the plurality of axes with a set of lines,
   wherein displaying further comprises displaying the lines.

6. The method of claim 5, wherein connecting further comprises connecting the identified points on the plurality of axes to delineate an area within the lines, and
   wherein displaying further comprises visually distinguishing the area from its surroundings.

* * * * *